(12) United States Patent
Kamal et al.

(10) Patent No.: US 8,063,204 B2
(45) Date of Patent: Nov. 22, 2011

(54) BENZOTHIAZOLE AND BENZOXAZOLE LINKED PYRROLO[2,1-C] [1, 4] BENZODIAZEPINE HYBRIDS AS NOVEL ANTITUMOUR AGENTS AND PROCESS FOR THE PREPARATION THEREOF

(75) Inventors: Ahmed Kamal, Hyderabad (IN); K. Srinivasa Reddy, Hyderabad (IN); Mohammed Naseer Ahmed Khan, Hyderabad (IN); Rajesh V. C. R. N. C Shetti, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 12/526,914

(22) PCT Filed: Dec. 31, 2007

(86) PCT No.: PCT/IN2007/000619
§ 371 (c)(1),
(2), (4) Date: Aug. 12, 2009

(87) PCT Pub. No.: WO2008/099416
PCT Pub. Date: Aug. 21, 2008

(65) Prior Publication Data
US 2010/0113771 A1    May 6, 2010

(30) Foreign Application Priority Data
Feb. 13, 2007    (IN) ............................. 277/DEL/2007

(51) Int. Cl.
*C07D 487/04*    (2006.01)
*A61K 31/5517*    (2006.01)
(52) U.S. Cl. ....................................................... 540/496
(58) Field of Classification Search ................... 540/496
See application file for complete search history.

(56) References Cited

U.S. PATENT DOCUMENTS
2005/0222133 A1    10/2005    Kamal et al.

FOREIGN PATENT DOCUMENTS
WO    2005/063759 A1    7/2005

*Primary Examiner* — Bruck Kifle
(74) *Attorney, Agent, or Firm* — Ladas & Parry LLP

(57) ABSTRACT

The present invention provides a compound of general formula (9), useful as potential antitumour agents against human cancer cell lines. The present invention further provides a process for the preparation of pyrrolo[2,1-c][1,4][benzodiazepine g hybrids of general formula (9).

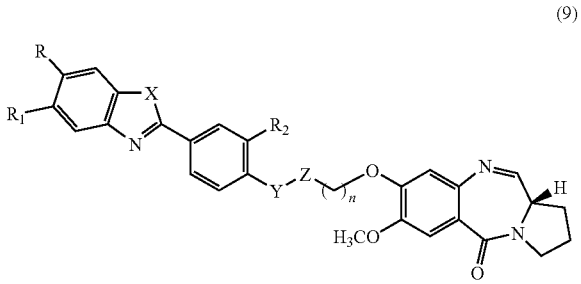

17 Claims, No Drawings

BENZOTHIAZOLE AND BENZOXAZOLE LINKED PYRROLO[2,1-C] [1, 4] BENZODIAZEPINE HYBRIDS AS NOVEL ANTITUMOUR AGENTS AND PROCESS FOR THE PREPARATION THEREOF

FIELD OF THE INVENTION

The present invention relates to novel benzothiazole or benzoxazole linked pyrrolo[2,1-c][1,4]benzodiazepine hybrid as potential antitumour agent. The present invention also relates to a process for the preparation of novel benzothiazole or benzoxazole linked pyrrolo[2,1-c][1,4]benzodiazepine hybrid.

More particularly, the present invention relates to benzothiazole or benzoxazole linked pyrrolo[2,1-c][1,4]benzodiazepine hybrid of general formula 9

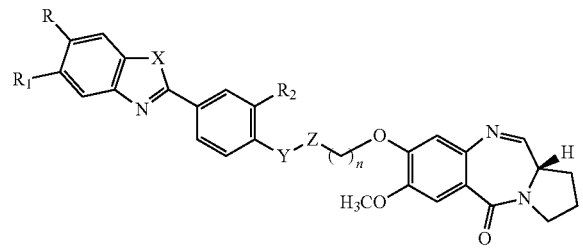

R, $R_1$ = H or F
$R_2$ = $OCH_3$ or H
X = S or O
Y = NH or O
Z = $CH_2$ or CO
n = 3-4

The present invention further relates to a process for the preparation of 7-methoxy-8-{n-[4-(1,3-benzothiazol-2-yl)-2-substituted phenoxy]alkyl}oxy-(11aS)-1,2,3,11a-tetrahydro-5H-pyrrolo[2,1-c][1,4]benzodiazepin-5-one/7-methoxy-8-{n-[4-(1,3-benzoxazol-2-yl)-2-substituted phenoxy]alkyl}oxy-(11aS)-1,2,3,11a-tetrahydro-5H-pyrrolo[2,1-c][1,4]benzodiazepin-5-one/7-methoxy-8-{n-[$N^1$-(4-(7-substituted-1,3-benzo thiazol-2-yl)phenyl]alkanecarboxamide}oxy-(11aS)-1,2,3,11a-tetrahydro-5H-pyrrolo[2,1-c][1,4]benzodiazepin-5-one with aliphatic chain length variations.

BACKGROUND OF THE INVENTION

Pyrrolo[2,1-c][1,4]benzodiazepines (PBDs), a group of potent naturally occurring antitumour antibiotics from various Streptomyces species, are of considerable interest because of their ability to recognize and subsequently form covalent bonds to specific base sequence of double strand DNA (Dervan, P. B. *Science* 1989, 232, 464.; Hurley, L. H. *J. Med. Chem.* 1989, 32, 2027.; Thurston, D. E.; Thompson, A. S. *Chem. Br.* 1990, 26, 767). Well-known members of this group include anthramycin, DC-81, sibiromycin, tomamycin, chicamycin and neothramycin of A and B (Hurley, L. H. *J. Antibiot.* 1977, 30, 349.; Schimizu, K.; Kawamoto, I.; Tomita, F.; Morimoto, M.; Fujimoto, K. *J. Antibiot.* 1982, 35, 992.; Lown, J. W.; Joshua, A. V. *Biochem. Pharmacol.* 1979, 28, 2017.; Thurston, D. E.; Bose, D. S. *Chem. Rev.* 1994, 94, 433.; Molina, P.; Diaz, I.; Tarraga, A. *Tetrahedron* 1995, 51, 5617.; Kamal, A.; Rao, N. V. *Chem. Commun.* 1996, 385.; Kamal, A.; Reddy, B. S. P.; Reddy, B. S. N. *Tetrahedron Lett.* 1996, 37, 6803). The cytotoxicity and antitumour activity of these agents are attributed to their property of sequence selective covalent binding to the N2 of guanine in the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. *J. Org. Chem.* 1996, 61, 8141).

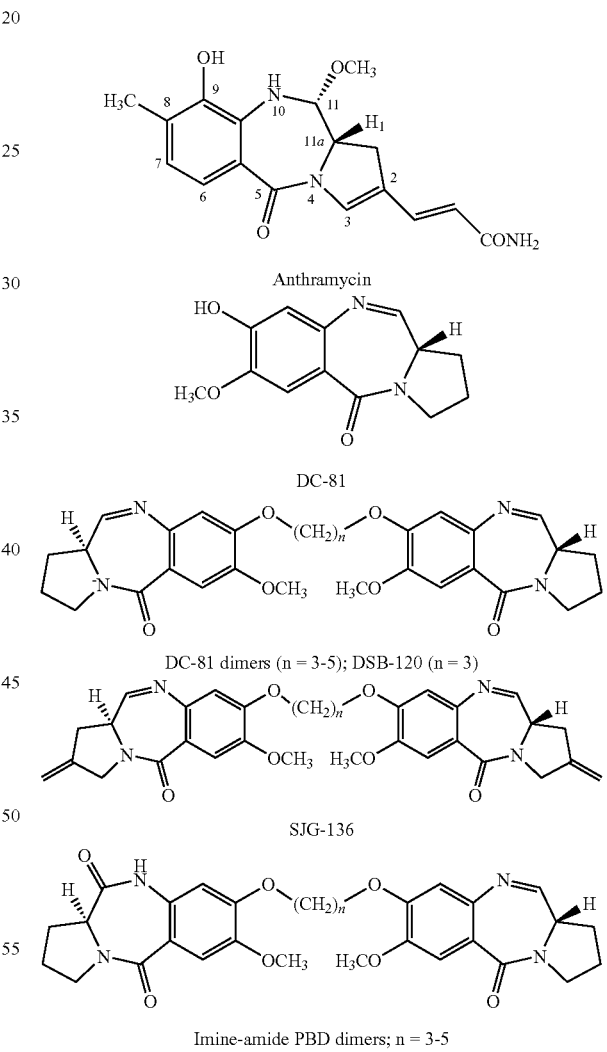

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). However, the clinical efficacy for these antibiotics is hindered by several limitations, such as poor water solubility, cardiotoxicity, development of drug resistance and metabolic inactivation. Due to the excellent activity of these molecules, there is need to develop novel derivatives which are devoid of above limitations.

Benzothiazoles are small synthetic molecules that contain a benzene ring fused to a thiazole ring. These simple molecules have shown remarkable antitumour properties and some of them are undergoing evaluation in clinical trials (Shi, D.-F.; Bradshaw, T. D.; Wrigley, S.; McCall, C. J.; Lelieveld, P.; Fichtner, I.; Stevens, M. F. G. *J. Med. Chem.* 1996, 39, 3375; Kashiyama, E.; Hutchinson, I.; Chua, M.-S.; Stinson, S. F.; Phillips, L. R.; Kaur, G.; Sausville, E. A.; Bradshaw, T. D.; Westwell, A. D.; Stevens, M. F. G. *J. Med. Chem.* 1999, 42, 4172; Hutchinson, I.; Chua, M.-S.; Browne, H. L.; Trapani, V.; Bradshaw, T. D.; Westwell, A. D.; Stevens, M. F. G. *J. Med. Chem.* 2001, 44, 1446). Recently Westwell and coworkers have prepared a series of benzothiazole derivatives and evaluated for anticancer activity, One of these analogues has shown excellent anticancer activity (Mortimer, C. G.; Wells, G.; Crochard, J.-P.; Stone, E. L; Bradshaw, T. D.; Stevens, M. F. G.; Westwell, A. D. *J. Med. Chem.* 2006, 49, 179). The structurally related benzoxazoles have also been reported to possess anticancer activity (Kumar, D.; Jacob, M. R.; Reynold, M. B.; Kerwin, S. M. *Bioorg. Med. Chem.* 2002, 10, 3994; Gong, B.; Hong, F.; Kohm, C.; Bonham, L.; Klein, P. *Bioorg. Med. Chem. Lett.* 2004, 14, 1455). Based on the potent anticancer activity of pyrrolo[2,1-c][1,4]benzodiazepines, benzothiazoles and benzoxazoles, new PBD hybrids have been designed and synthesized by linking benzothiazole and benzoxazole moieties at C8-position of pyrrolo[2,1-c][1,4]benzodiazepine with varying alkane and alkylamide spacers.

OBJECTIVES OF THE INVENTION

The main objective of the present invention is to provide novel benzothiazole or benzoxazole linked pyrrolo[2,1-c][1,4]benzodiazepine hybrid useful as antitumour agent.

Yet another object of the present invention is to provide a process for the preparation of novel benzothiazole or benzoxazole linked pyrrolo[2,1-c][1,4]benzodiazepine hybrids.

SUMMARY OF THE INVENTION

Accordingly the present invention provides novel benzothiozole or benzoxazole linked pyrrolo[2,1-c][1,4]benzodiazepines of formula 9, Formula 9

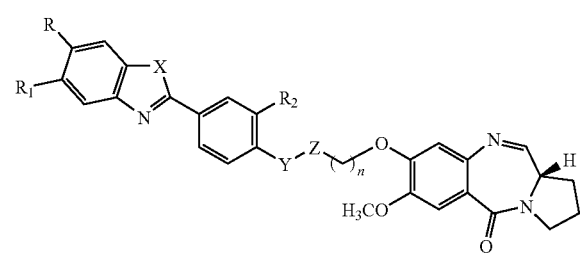

Wherein: n=3-4, X=S or O; Y=NH or O; Z=CO or CH$_2$; R, R$_1$=H or F; R$_2$=OCH$_3$ or H.

In an embodiment of the present invention the representative compounds of formula 9 are as follows:

7-Methoxy-8-{-4-[4-(1,3-benzothiazol-2-yl)phenoxy]butyl}oxy-(11aS)-1,2,3,11a-tetrahydro-5H-pyrrolo[2,1-c][1,4]benzodiazepin-5-one (9a);

7-Methoxy-8-{4-[4-(1,3-benzothiazol-2-yl)-2-methoxyphenoxy]butyl}oxy-(11aS)-1,2,3,11a-tetrahydro-5H-pyrrolo[2,1-c][1,4]benzodiazepin-5-one (9b);

7-Methoxy-8-{5-[4-(1,3-benzothiazol-2-yl)phenoxy]pentyl}oxy-(11aS)-1,2,3,11a-tetrahydro-5H-pyrrolo[2,1-c][1,4]benzodiazepin-5-one (9c);

7-Methoxy-8-{5-[4-(1,3-benzothiazol-2-yl)-2-methoxyphenoxy]pentyl}oxy-(11aS)-1,2,3,11a-tetrahydro-5H-pyrrolo[2,1-c][1,4]benzodiazepin-5-one (9d);

7-Methoxy-8-{5-[4-(1,3-benzoxazol-2-yl)phenoxy]pentyl}oxy-(11aS)-1,2,3,11a-tetra-hydro-5H-pyrrolo[2,1-c][1,4]benzodiazepin-5-one (9e);

7-Methoxy-8-{5-[4-(1,3-benzoxazol-2-yl)-2-methoxyphenoxy]pentyl}oxy-(11aS) 1,2,3,11a-tetra-hydro-5H-pyrrolo[2,1-c][1,4]benzodiazepin-5-one (9f);

7-Methoxy-8-{5-[N$^1$-(4-(1,3-benzothiazol-2-yl)phenyl)]pentanecarboxamide}oxy-(11aS)-1,2,3,11a-tetra-hydro-5H-pyrrolo[2,1-c][1,4]benzodiazepin-5-one (9g); and 7-Methoxy-8-{5-[N$^1$-(4-(6-fluoro-1,3-benzothiazol-2-yl)phenyl)]pentane carboxamide}oxy-(11aS)-1,2,3,11a-tetra-hydro-5H-pyrrolo[2,1-c][1,4]benzodiazepin-5-one (9h).

In yet another embodiment the structural formula of the representative compounds 9a-h are:

(9a)

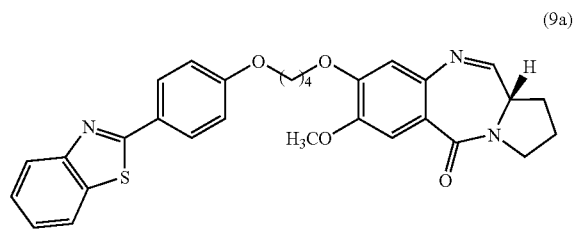

(9b)

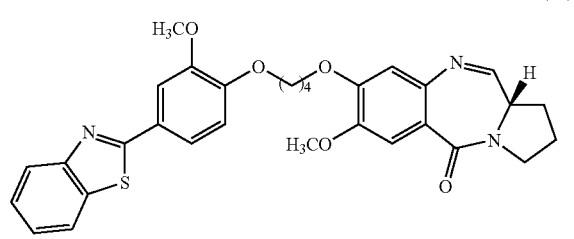

(9c)

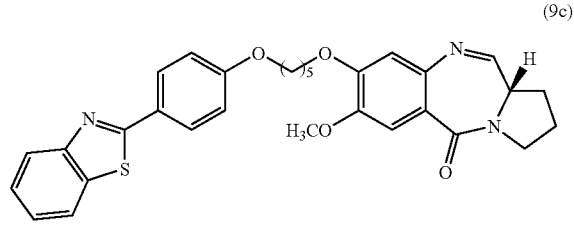

-continued

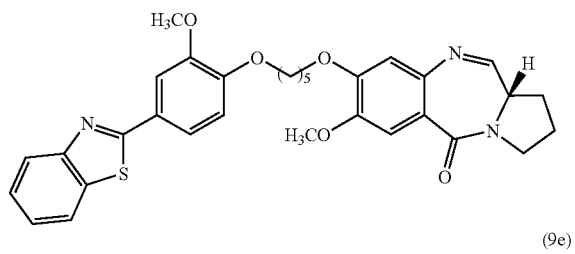
(9d)

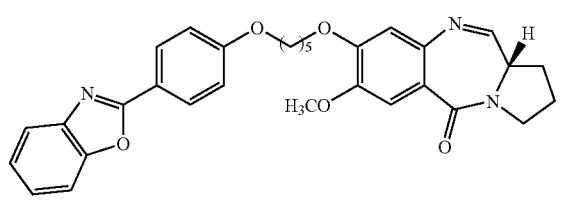
(9e)

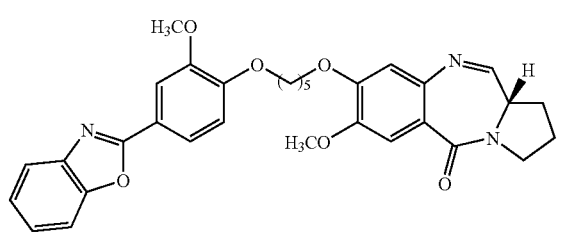
(9f)

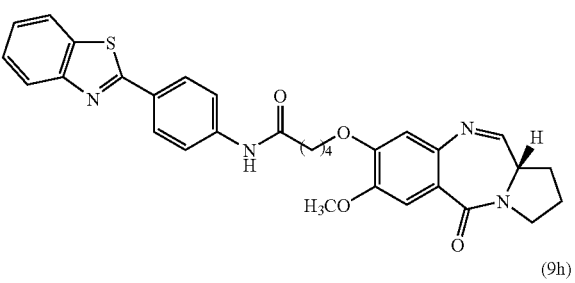
(9g)

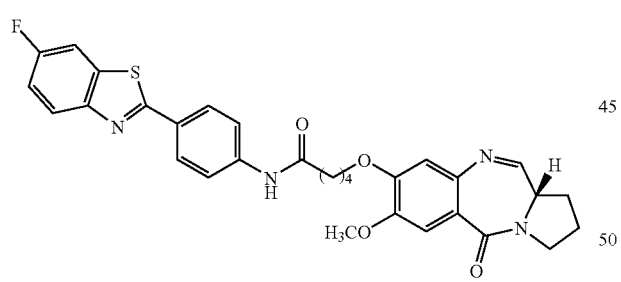
(9h)

In yet another embodiment the compounds of formula 9 exhibits binding affinity with calf thymus (CT) DNA at a molar ratio of 1:5 in aqueous sodium phosphate buffer at pH 7.

In yet another embodiment the compounds of formula 9 exhibit in-vitro cytotoxicity against human tumor cells derived from nine cancer types of leukemia, non-small-cell lung, colon, CNS, melanoma, ovarian, prostate, and breast cancer.

In yet another embodiment the compound 9a exhibits in-vitro cytotoxicity in mean graph midpoint value of −6.30 (mol/lit), −5.63 (mol/lit), and −4.75 (mol/lit) for $\log_{10}$ GI50, $\log_{10}$ TGI and $\log_{10}$ LC50, respectively, against nine human tumor cell lines.

In yet another embodiment the compound 9b exhibits in-vitro cytotoxicity in mean graph midpoint value of $\log_{10}$ TGI, $\log_{10}$ LC50, $\log_{10}$ GI50. In-vitro cytotoxicity data in mean graph midpoint value of −6.07, −5.47, and −4.67 for $\log_{10}$ GI50, $\log_{10}$ TGI and $\log_{10}$ LC50, respectively, against nine human tumor cell lines.

In yet another embodiment the compound 9c exhibits in-vitro cytotoxicity in mean graph midpoint value of −6.15, −5.30, and −4.35 for $\log_{10}$ GI50, $\log_{10}$ TGI and $\log_{10}$ LC50, respectively, against nine human tumor cell lines.

In yet another embodiment the compound 9d exhibits in-vitro cytotoxicity in mean graph midpoint value of −7.09, −5.78, and −4.37 for $\log_{10}$ GI50, $\log_{10}$ TGI and $\log_{10}$ LC50, respectively, against nine human tumor cell lines.

In yet another embodiment the compound 9a exhibits $\log_{10}$ GI50 (mole/lit) anticancer activity against nine cancer cell type in the range of −6.08 to −6.73.

In yet another embodiment the compound 9b exhibits $\log_{10}$ GI50 (mole/lit) anticancer activity against nine cancer cell type in the range of −5.85 to −6.45.

In yet another embodiment the compound 9c exhibits $\log_{10}$ GI50 (mole/lit) anticancer activity against nine cancer cell type in the range of −5.87 to −6.65.

In yet another embodiment the compound 9d exhibits $\log_{10}$ GI50 (mole/lit) anticancer activity against nine cancer cell type in the range of −6.79 to −7.51.

The present invention further provides a process for the preparation of novel benzothiazole or benzoxazole linked pyrrolo[2,1-c][1,4]benzodiazepines of formula 9,

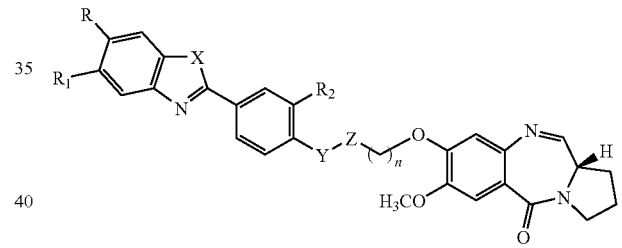

wherein: 'n' is 3-4, X=S or O; Y=NH or O; Z=CO or $CH_2$; R, $R_1$=H or F; $R_2$=$OCH_3$ or H and the said process comprising the steps of:

a) reacting a compound of formula 1 or formula 2

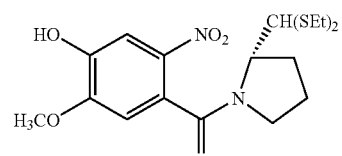
1

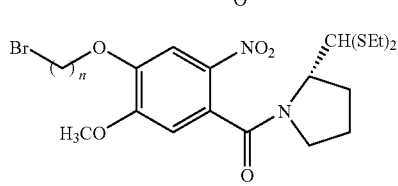
2a-b 2a (n = 3)
2b (n = 4)

with benzothiazole or benzoxazole derivative selected from the compounds of formula 3 and 6,

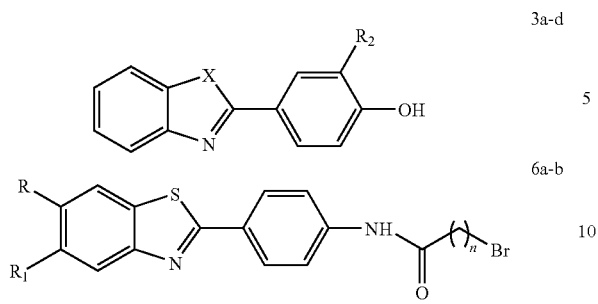
in the presence of K$_2$CO$_3$, in organic solvent, under refluxing temperature to obtain the resultant nitro compound of formula 4 or 7;
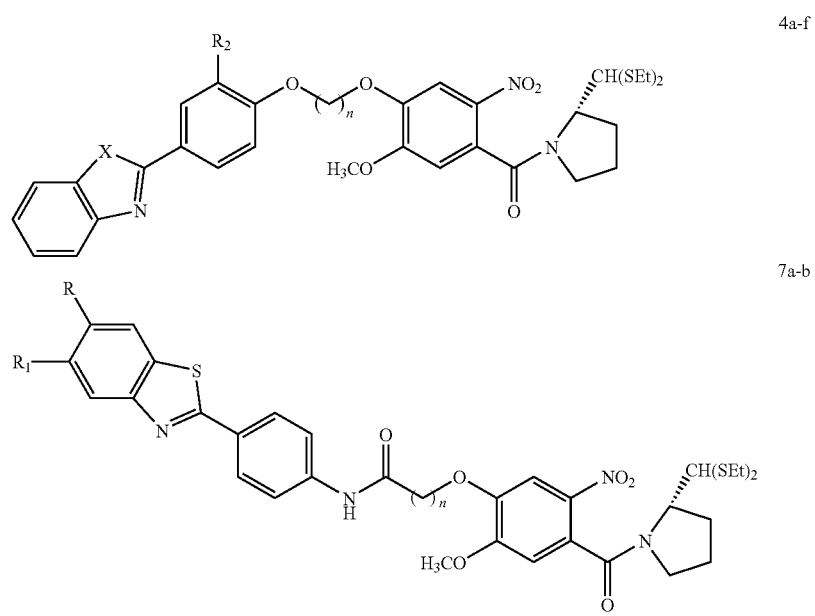
b) reducing the above said nitro compound of formula 4 or 7 obtained in step (a) with SnCl$_2$.2H$_2$O in an organic solvent, under reflux temperature and isolating the corresponding amino compound of formula 5 or 8, respectively, and
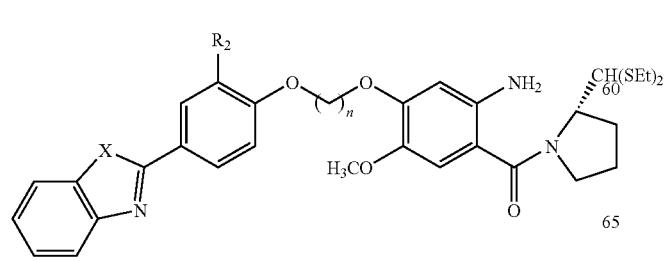

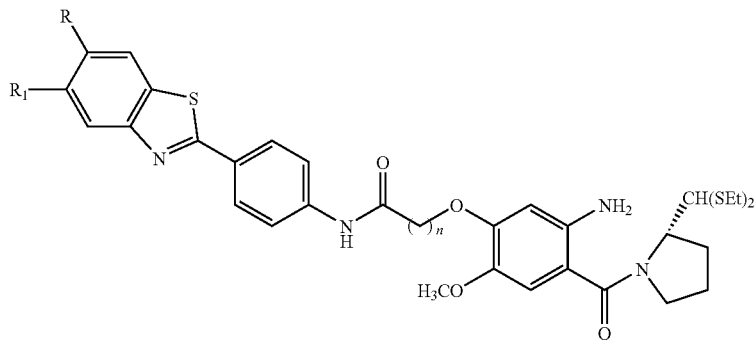

8a-b c) reacting the above said amino compound of formula 5 or 8 obtained in step (b) with a deprotecting agent by known method to obtain the desired compound of formula 9.

In yet another embodiment the organic solvent used in step (a) is acetone and in step (b) is ethanol or methanol In yet another embodiment in step (a) the compound of formula 2 is reacted with benzothiazole or benzoxazole derivative of formula 3 to obtain the resultant nitro compound of formula 4.

In yet another embodiment in step (a) the compound of formula 1 is reacted with benzothiazole or benzoxazole derivative of formula 6 to obtain the resultant nitro compound of formula 7.

In yet another embodiment the compound of formula 1 used in step (a) is (2S)—N-[4-hydroxy-5-methoxy-2-nitrobenzoyl]pyrrolidine-2-carboxaldehyde diethylthioacetal.

In yet another embodiment the compound of formula 2 used in step (a) is selected from (2S)—N-[4-(3-bromobutyl)oxy-5-methoxy-2-nitrobenzoyl)pyrrolidine-2-carboxarbaldehyde diethylthioacetal (2a) and (2S)—N-[4-(5-bromopentyloxy)-5-methoxy-2-nitrobenzoyl]pyrrolidine-2-carboxaldehyde diethylthioacetal (2b).

In yet another embodiment in step (a) the compound of formula 3 used is selected from the group consisting of 4-(benzothiazol-2-yl)phenol (3a), 4-(1,3-benzothiazol-2-yl)-2-methoxyphenol (3b), 4-(benzoxazol-2-yl)phenol (3c), and 4-(1,3-benzoxazol-2-yl)-2-methoxyphenol (3d).

In yet another embodiment in step (a) the compound of formula 4 obtained is selected from the group consisting of (2S)—N-{4-(n-[4-(1,3-benzothiazol-2-yl)phenoxy]butyl)oxy-5-methoxy-2-nitrobenzoyl}-pyrrolidine-2-carboxaldehyde diethylthioacetal (4a), (2S)—N-{4-(n-[4-(1,3-benzothiazol-2-yl)-2-methoxyphenoxy]butyl)oxy-5-methoxy-2-nitrobenzoyl}-pyrrolidine-2-carboxaldehyde diethylthioacetal (4b), (2S)—N-{4-(n-[4-(1,3-benzothiazol-2-yl)phenoxy]pentyl)oxy-5-methoxy-2-nitrobenzoyl}-pyrrolidine-2-carboxaldehyde diethylthio acetal (4c), (2S)—N-{4-(n-[4-(1,3-benzothiazol-2-yl)-2-methoxyphenoxy]pentyl)oxy-5-methoxy-2-nitrobenzoyl}-pyrrolidine-2-carboxaldehydediethylthioacetal (4d), (2S)—N-{4-(n-[4-(1,3-benzoxozol-2-yl)phenoxy]pentyl)oxy-5-methoxy-2-nitrobenzoyl}-pyrrolidine-2-carboxaldehyde diethylthioacetal (4e) and (2S)—N-{4-(n-[4-(1,3-benzoxozole-2-yl)-2-methoxyphenoxy]pentyl)oxy-5-methoxy-2-nitrobenzoyl}-pyrrolidine-2-carboxaldehyde diethylthioacetal (4f).

In yet another embodiment in step (b) the compound of formula 5 obtained is selected from the group consisting of (2S)—N-{4-(n-[4-(1,3-benzothiazol-2-yl)phenoxy]butyl) oxy-5-methoxy-2-aminobenzoyl}-pyrrolidine-2-carboxaldehyde diethylthioacetal (5a), (2S)—N-{4-(n-[4-(1,3-benzothiazol-2-yl)-2-methoxyphenoxy]butyl)oxy-5-methoxy-2-aminobenzoyl}-pyrrolidine-2-carboxaldehyde diethylthioacetal (5b), (2S)—N-{4-(n-[4-(1,3-benzothiazol-2-yl)phenoxy]pentyl)oxy-5-methoxy-2-aminobenzoyl}-pyrrolidine-2-carboxaldehyde diethyl thioacetal (5c), (2S)—N-{4-(n-[4-(1,3-benzothiazol-2-yl)-2-methoxy phenoxy]pentyl)oxy-5-methoxy-2-aminobenzoyl}-pyrrolidine-2-carboxaldehyde diethyl thioacetal (5d), (2S)—N-{4-(n-[4-(1,3-benzoxozol-2-yl)phenoxy]pentyl)oxy-5-methoxy-2-aminobenzoyl}-pyrrolidine-2-carboxaldehyde diethylthioacetal (5e) and (2S)—N-{4-(n-[4-(1,3-benzxozole-2-yl)-2-methoxyphenoxy]pentyl)oxy-5-methoxy-2-aminobenzoyl}-pyrrolidine-2-carboxaldehyde diethylthioacetal (5f).

In yet another embodiment the compound of formula 6 used in step (a) is selected from N1-[4-(1,3-benzothiazol-2-yl)phenyl]-5-bromopentanamide (6a) or N1-[4-(6-fluoro-1,3-benzothiazol-2-yl)phenyl]-5-bromopentanamide (6b).

In yet another embodiment the compound of formula 7 obtained in step (a) is selected from (2S)—N-{4-(5-[N$^1$-(4-(1,3-benzothiazol-2-yl)phenyl)]-pentanecarboxamide)oxy-5-methoxy-2-nitrobenzoyl}-pyrrolidine-2-carboxaldehyde diethylthioacetal (7a) or (2S)—N-{4-(5-[N$^1$-(4-(6-fluoro-1,3-benzothiazol-2-yl)phenyl)-pentanecarboxamide]oxy)-5-methoxy-2-nitrobenzoyl}-pyrrolidine-2-carboxaldehyde diethylthioacetal (7b).

In yet another embodiment the compound of formula 8 obtained in step (b) is selected from the group consisting of (2S)—N-{4-(n-[4-(1,3-benzothiazol-2-yl)phenoxy]butyl)oxy-5-methoxy-2-aminobenzoyl}-pyrrolidine-2-carboxaldehyde diethyl thioacetal (8a) and (2S)—N-{4-(n-[4-(1,3-benzothiazol-2-yl)-2-methoxyphenoxy]pentyl)oxy-5-methoxy-2-aminobenzoyl}-pyrrolidine-2-carboxaldehyde diethylthioace (8b).

In yet another embodiment the representative compounds of formula 9 obtained in step (c) are as follows:

7-Methoxy-8-{4-[4-(1,3-benzothiazol-2-yl)phenoxy]butyl}oxy-(11aS)-1,2,3,11a-tetrahydro-5H-pyrrolo[2,1-c][1,4]benzodiazepin-5-one (9a);

7-Methoxy-8-{4-[4-(1,3-benzothiazol-2-yl)-2-methoxyphenoxy]butyl}oxy-(11aS)-1,2,3,11a-tetrahydro-5H-pyrrolo[2,1-c][1,4]benzodiazepin-5-one (9b);

7-Methoxy-8-{5-[4-(1,3-benzothiazol-2-yl)phenoxy]pentyl}oxy-(11aS)-1,2,3,11a-tetrahydro-5H-pyrrolo[2,1-c][1,4]benzodiazepin-5-one (9c);

7-Methoxy-8-{5-[4-(1,3-benzothiazol-2-yl)-2-methoxyphenoxy]pentyl}oxy-(11aS)-1,2,3,11a-tetrahydro-5H-pyrrolo[2,1-c][1,4]benzodiazepin-5-one (9d);

7-Methoxy-8-{5-[4-(1,3-benzoxazol-2-yl)phenoxy]pentyl}oxy-(11aS) 1,2,3,11a-tetra-hydro-5H-pyrrolo[2,1-c][1,4]benzodiazepin-5-one (9e);

7-Methoxy-8-{5-[4-(1,3-benzoxazol-2-yl)-2-methoxyphenoxy]pentyl}oxy-(11aS) 1,2,3,11a-tetra-hydro-5H-pyrrolo[2,1-c][1,4]benzodiazepin-5-one (9f);

7-Methoxy-8-{5-[N$^1$-(4-(1,3-benzothiazol-2-yl)phenyl)]pentanecarboxamide}oxy-(11aS)-1,2,3,11a-tetra-hydro-5H-pyrrolo[2,1-c][1,4]benzodiazepin-5-one (9g) and 7-Methoxy-8-{5-[N$^1$-(4-(6-fluoro-1,3-benzothiazol-2-yl)phenyl)]pentane carboxamide}oxy-(11aS)-1,2,3,11a-tetra-hydro-5H-pyrrolo[2,1-c][1,4]benzodiazepin-5-one (9h).

DETAILED DESCRIPTION OF THE INVENTION

The precursors 4-(1,3-benzothiazol-2-yl)phenol/4-(1,3-benzothiazol-2-yl)-2-methoxyphenol of formula 3a-b (Ben-Allum, A.; Bakkas, S.; Soufiaoui, M. *Tetrahedron Lett.* 1997, 38, 6395; Wells, G.; Lowe, P. R.; Stevens, M. F. G. *ARKIVOC* 2000, 1, 779) and (2S)—N-[4-(hydroxy-5-methoxy-2-nitrobenzoyl]pyrrolidine-2-carboxaldehyde diethylthioacetal of formula 2 (Thurston, D. E.; Murthy, V. S.; Langley, D. R.; Jones, G. B. *Synthesis*. 1990, 81) have been prepared by literature methods. The benzoxazole precursors 3c-d have been prepared by condensation of 2-aminophenols with benzylated protected benzaldehydes, oxidation followed by debenzylation with palladium on charcoal (Centore, R.; Panunzi, B.; Roviello, A.; Sirigu, A.; Villano, P. *J. Polym. Sci Part A: Polym. Chem.* 1996, 34, 3203). Amide derivatives of benzothiazoles of formula 6a-b have been prepared by coupling bromoacid chlorides with corresponding 2-(4-aminophenyl)benzothiazoles.

Some representative compounds of formula 9 for the present inventions are given below a) 7-Methoxy-8-{4-[4-(1,3-benzothiazol-2-yl)phenoxy]butyl}oxy-(11aS)-1,2,3,11a-tetrahydro-5H-pyrrolo[2,1-c][1,4]benzodiazepin-5-one b) 7-Methoxy-8-{4-[4-(1,3-benzothiazol-2-yl)-2-methoxyphenoxy]butyl}oxy-(11aS)-1,2,3,11a-tetrahydro-5H-pyrrolo[2,1-e][1,4]benzodiazepin-5-one c) 7-Methoxy-8-{5-[4-(1,3-benzothiazol-2-yl)phenoxy]pentyl}oxy-(11aS)-1,2,3,11a-tetrahydro-5H-pyrrolo[2,1-c][1,4]benzodiazepin-5-one d) 7-Methoxy-8-{5-[4-(1,3-benzothiazol-2-yl)-2-methoxyphenoxy]pentyl}oxy-(11aS)-1,2,3,11a-tetrahydro-5H-pyrrolo[2,1-c][1,4]benzodiazepin-5-one e) 7-Methoxy-8-{5-[4-(1,3-benzoxazol-2-yl)phenoxy]pentyl}oxy-(11aS) 1,2,3,11a-tetra-hydro-5H-pyrrolo[2,1-c][1,4]benzodiazepin-5-one f) 7-Methoxy-8-{5-[4-(1,3-benzoxazol-2-yl)-2-methoxyphenoxy]pentyl}oxy-(11aS) 1,2,3,11a-tetra-hydro-5H-pyrrolo[2,1-c][1,4]benzodiazepin-5-one g) 7-Methoxy-8-{5-[N$^1$-(4-(1,3-benzothiazol-2-yl)phenyl)]pentanecarboxamide}oxy-(11aS)-1,2,3,11a-tetra-hydro-5H-pyrrolo[2,1-c][1,4]benzodiazepin-5-one h) 7-Methoxy-8-{5-[N$^1$-(4-(6-fluoro-1,3-benzothiazol-2-yl)phenyl)]pentane carboxamide}oxy-(11aS)-1,2,3,11a-tetra-hydro-5H-pyrrolo[2,1-c][1,4]benzodiazepin-5-one These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This present invention is illustrated in Scheme 1 and scheme 2 as herein given below:

1) The ether linkage at C-8 position of DC-81 intermediates with benzothiazole and benzoxazole moieties.
2) Refluxing the reaction mixtures for 48 h.
3) Synthesis of C-8 linked PBD antitumour antibiotic hybrid imines.
4) Purification by column chromatography using different solvents like ethyl acetate, hexane, chloroform and methanol.

Representative Compounds 9a-h of General Structural Formula 9

| Compound | R | R$_1$ | R$_2$ | X | Y | Z | n |
|---|---|---|---|---|---|---|---|
| 9a | H | H | H | S | O | CH$_2$ | 3 |
| 9b | H | H | OCH$_3$ | S | O | CH$_2$ | 3 |
| 9c | H | H | H | S | O | CH$_2$ | 4 |
| 9d | H | H | OCH$_3$ | S | O | CH$_2$ | 4 |
| 9e | H | H | H | O | O | CH$_2$ | 4 |
| 9f | H | H | H | O | O | CH$_2$ | 4 |
| 9g | H | H | H | S | NH | CO | 4 |
| 9h | H | F | H | S | NH | CO | 4 |

Scheme 1

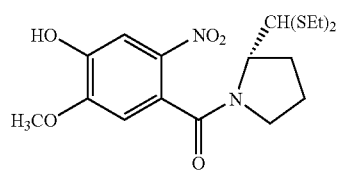

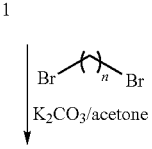

K$_2$CO$_3$/acetone

-continued
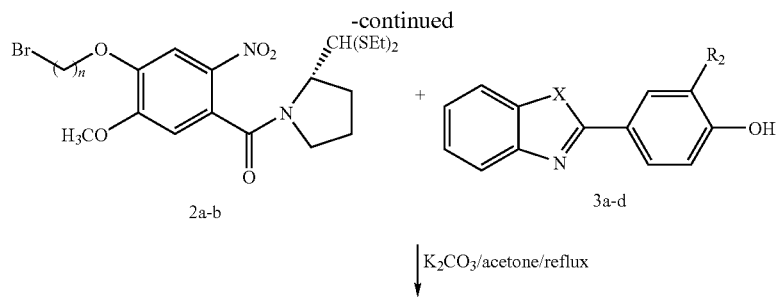
2a-b + 3a-d
↓ K₂CO₃/acetone/reflux
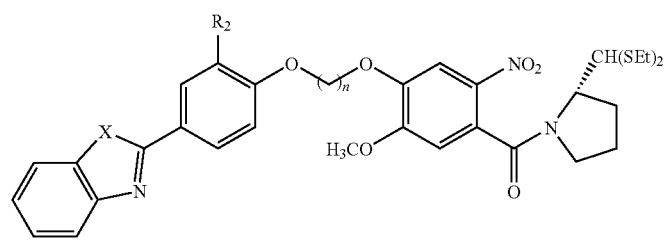
4a-f
↓ SnCl₂·2H₂O/methanol
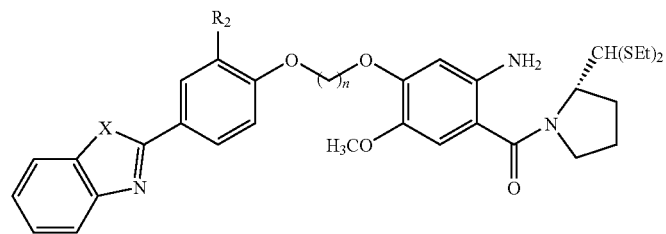
5a-f
↓ HgCl₂/CaCO₃
CH₃CN—H₂O
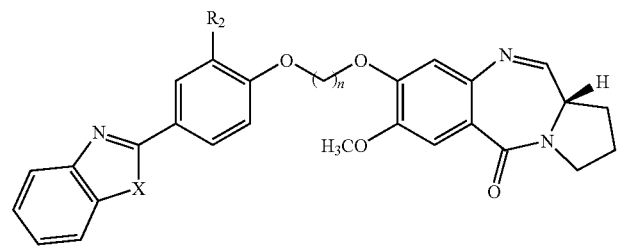
9a-f
X = O, S
R₂ = OCH₃, H
n = 4, 5

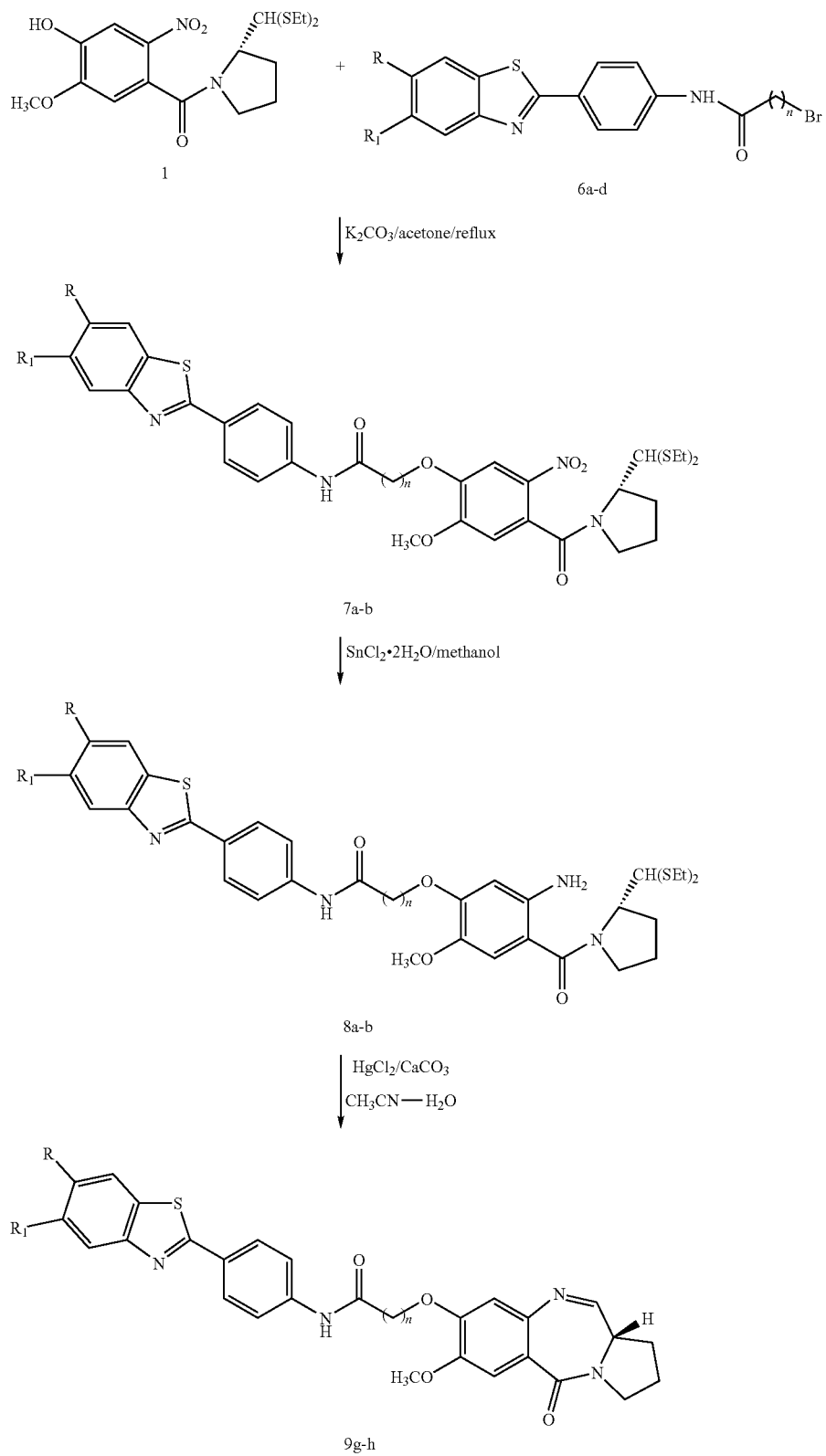
Scheme 2
7a-b
8a-b
9g-h
R, R₁ = H, F
n = 4

The following examples are given by way of illustration of the working of the invention in actual practice and therefore should not be construed to limit the scope of present invention in any way.

EXAMPLE 1

To a solution of (2S)—N-[4-(3-bromobutyl)oxy-5-methoxy-2-nitrobenzoyl)pyrrolidine-2-carboxarbaldehyde diethylthioacetal 2a (535 mg, 1 mmol) in acetone (10 mL) was added anhydrous $K_2CO_3$ (552 mg, 4 mmol) and the 4-(benzothiazol-2-yl)phenol 3a (227 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (1:1) as eluant to afford pure compound of 4a (511 mg, 75%).

$^1$H NMR (CDCl$_3$): δ 8.0 (d, 2H, J=8.8 Hz), 7.9 (d, 1H, J=8 Hz), 7.7 (s, 1H), 7.3-7.5 (m, 3H), 7.0 (d, 2H, J=8.8 Hz), 6.8 (s, 1H), 4.9 (d, 1H, J=3.7 Hz), 4.7 (m, 1H), 4.2 (m, 4H), 3.90 (s, 3H), 3.2 (m, 2H), 2.7-2.9 (m, 4H), 1.7-2.3 (m, 8H), 1.2-1.4 (m, 6H).

ESIMS: m/z 683 (M$^+$+1).

To compound 4a (682 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 5a (522 mg, 80%), which was used directly in the next step.

A solution of 5a (652 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 9a (316 mg, 60%). This material was repeatedly evaporated from CHCl$_3$ in vacuum to generate the imine form.

$^1$H NMR (CDCl$_3$): δ 8.0 (d, 2H, J=8.8 Hz), 7.9 (d, 1H, J=8 Hz), 7.65 (d, 1H, J=4.0 Hz), 7.5 (s, 1H), 7.3-7.45 (m, 3H), 7.0 (d, 2H, J=8.8 Hz), 6.8 (s, 1H), 4.1 (m, 4H), 3.90 (s, 3H), 3.5-3.85 (m, 3H), 1.9-2.3 (m, 8H).

FABMS: 528 (M$^+$+1).

EXAMPLE 2

To a solution of (2S)—N-[4-(3-bromobutyl)oxy-5-methoxy-2-nitrobenzoyl)pyrrolidine-2-carboxarbaldehyde diethylthioacetal 2a (535 mg, 1 mmol) in acetone (10 mL) was added anhydrous $K_2CO_3$ (552 mg, 4 mmol) and the 4-(1,3-benzothiazol-2-yl)-2-methoxyphenol 3b (257 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (3:2) as eluant to afford pure compound of 4b $^1$H NMR (CDCl$_3$): δ 8.0 (d, 1H, J=8.8 Hz), 7.85 (d, 1H, J=8.8 Hz), 7.7 (m, 2H), 7.5 (dd, 1H, J=1.6 Hz), 7.45 (t, 1H, J=8 Hz), 7.3 (t, 1H, J=8 Hz), 6.90 (d, 1H, J=8.8 Hz), 6.7 (s, 1H), 4.8 (d, 1H, J=3.9 Hz), 4.65 (m, 1H), 4.2 (m, 4H), 4.0 (s, 3H), 3.9 (s, 3H), 3.2 (m, 2H), 2.6-2.8 (m, 4H), 1.8-2.4 (m, 8H), 1.2-1.4 (m, 6H).

FABMS: m/z 712 (M$^+$).

To compound 4b (712 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 5b (511 mg, 75%), which was used directly in the next step.

A solution of 5b (682 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 9b (312 mg, 56%). This material was repeatedly evaporated from CHCl$_3$ in vacuum to generate the imine form.

$^1$H NMR (CDCl$_3$): δ 8.05 (d, 1H, J=7.8 Hz), 7.9 (d, 1H, J=7.8 Hz), 7.64-7.72 (m, 2H), 7.3-7.6 (m, 4H), 6.9 (d, 1H, J=7.8 Hz), 6.82 (s, 1H), 4.1-4.4 (m, 4H), 4.0 (s, 3H), 3.9 (s, 3H), 3.5-3.85 (m, 3H), 2.0-2.3 (m, 8H).

FABMS: m/z 558 (M$^+$+1).

EXAMPLE 3

To a solution of (2S)—N-[4-(5-bromopentyloxy)-5-methoxy-2-nitro benzoyl]pyrrolidine-2-carboxaldehyde diethylthioacetal 2b (549 mg, 1 mmol) in acetone (10 mL) was added anhydrous $K_2CO_3$ (552 mg, 4 mmol and the 4-(benzothiazol-2-yl)phenol 3a (227 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (1:1) as eluant to afford pure compound of 4c (522 mg, 75%).

$^1$H NMR (CDCl$_3$): δ 8.1 (d, 2H, J=8.8 z), 7.7-7.9 (m, 2H) 7.3-7.5 (m, 3H), 7.0 (d, 2H, J=8.8 Hz), 6.75 (s, 1H), 4.85 (d, 1H, J=3.8 Hz), 4.75 (m, 1H), 4.15 (m, 4H), 4.0 (s, 3H), 3.2 (m, 2H), 2.6-2.8 (m, 4H), 2.3 (m, 2H), 2.0 (m, 5H), 1.6-1.8 (m, 3H), 1.35 (q, 6H, J=7.5 Hz).

FABMS: m/z 696 (M$^+$).

To compound 4c (696 mg, 1 mmol) in methanol (20 mL) was added SnCl$_2$.2H$_2$O (1.125 g, 5 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethyl thioacetal 5c (533 mg, 80%), which was used directly in the next step.

A solution of 5c (666 mg, 1 mmol), HgCl$_2$ (613 mg, 2.26 mmol) and CaCO$_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (4%) to give compound 9c (323 mg, 60%). This material was repeatedly evaporated from CHCl₃ in vacuum to generate the imine form.

$^1$H NMR (CDCl₃): δ 8.0 (d, 1H, J=8.6 Hz), 7.85 (d, 1H, J=8.6 Hz), 7.65 (d, 1H, J=3.9 Hz), 7.3-7.55 (m, 5H), 7.0 (d, 2H, J=8.6 Hz), 6.82 (s, 1H), 4.0-4.2 (m, 4H), 3.9 (s, 3H), 3.6-3.8 (m, 3H), 2.2-2.4 (m, 2H), 1.8-2.0 (m, 5H), 1.6-1.8 (m. 3H).

FABMS: m/z 542 (M$^+$+1).

EXAMPLE 4

To a solution of (2S)—N-[4-(5-bromopentyloxy)-5-methoxy-2-nitrobenzoyl]pyrrolidine-2-carboxaldehyde diethylthioacetal 2b (549 mg, 1 mmol) in acetone (10 mL) was added anhydrous K₂CO₃ (552 mg, 4 mmol) and the 4-(1,3-benzothiazol-2-yl)-2-methoxyphenol 3b (257 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (3:2) as eluant to afford pure compound of 4d (508 mg, 70%).

$^1$H NMR (CDCl₃): δ 8.0 (d, 1H, J=8.7 Hz), 7.85 (d, 1H, J=8.7 Hz), 7.7 (d, 1H, J=1.6 Hz), 7.65 (s, 1H), 7.53 (dd, 1H, J=1.6, 8 Hz), 7.45 (dt, 1H, J=1.6, 8 Hz), 7.33 (dt, 1H, J=1.6, 8 Hz), 6.90 (d, 1H, J=8.7 Hz), 6.78 (s, 1H), 4.85 (d, 1H, J=3.9 Hz), 4.7 (m, 1H), 4.1 (m, 4H), 4.0 (s, 3H), 3.9 (s, 3H), 3.2 (m, 2H), 2.6-2.8 (m, 4H), 1.7-2.3 (m, 10H), 1.2-1.4 (m, 6H).

FABMS: m/z 726 (M$^+$).

To compound 4d (726 mg, 1 mmol) in methanol (20 mL) was added SnCl₂.2H₂O (1.125 g, 5 mmol) and refluxed for 5 h or until the TLC indicated that reaction was completed. The methanol was evaporated under vacuum, the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethyl thioacetal 5d (557 mg, 80%), which was used directly in the next step.

A solution of 5d (696 mg, 1 mmol), HgCl₂ (613 mg, 2.26 mmol) and CaCO₃ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 9d (314 mg, 55%). This material was repeatedly evaporated from CHCl₃ in vacuum to generate the imine form.

$^1$H NMR (CDCl₃): δ 8.0 (d, 1H, J=8.2 Hz), 7.9 (d, 1H, J=8.2 Hz), 7.64-7.72 (m, 2H), 7.3-7.6 (m, 4H), 6.95 (d, 1H, J=8.2 Hz), 6.80 (s, 1H), 4.1 (m, 4H), 4.0 (s, 3H), 3.95 (s, 3H), 3.5-3.8 (m, 3H), 1.7-2.3 (m, 10H).

FABMS: m/z 572 (M$^+$+1).

EXAMPLE 5

To a solution of (2S)—N-[4-(5-bromopentyloxy)-5-methoxy-2-nitrobenzoyl]pyrrolidine-2-carboxaldehyde diethylthioacetal 2b (549 mg, 1 mmol) in acetone (10 mL) was added anhydrous K₂CO₃ (552 mg, 4 mmol) and the 4-(benzoxazol-2-yl)phenol 3d (212 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (2:3) as eluant to afford pure compound of 4e (533 mg, 80%).

$^1$H NMR (CDCl₃): δ 8.05 (d, 2H, J=8.9 Hz), 7.6 (m, 1H), 7.5 (s, 1H), 7.4 (m, 1H), 7.2 (m, 2H), 6.9 (d, 2H, J=8.9 Hz), 6.64 (s, 1H), 4.7 (d, 1H, J=3.8 Hz), 4.55 (m, 1H), 4.0 (m, 4H), 3.80 (s, 3H), 3.1 (m, 2H), 2.52-2.8 (m, 4H), 1.5-2.1 (m, 10H), 1.2 (q, 6H, J=7.4 Hz).

LCMS: m/z 680 (M$^+$+1).

To compound 4e (665 mg, 1 mmol) in methanol (20 mL) was added SnCl₂.2H₂O (1.125 g, 5 mmol) and refluxed for 5 h or until the TLC indicated that reaction was completed. The methanol was evaporated under vacuum, the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethylthioacetal 5e which was used directly in the next step.

A solution of 5e (649 mg, 1 mmol), HgCl₂ (613 mg, 2.26 mmol) and CaCO₃ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (4%) to give compound 9e (263 mg, 50%). This material was repeatedly evaporated from CHCl₃ in vacuum to generate the imine form.

$^1$H NMR (CDCl₃): δ 8.2 (d, 2H, J=8.6 Hz), 7.72 (m, 1H), 7.65 (d, 1H, J=3.9 Hz), 7.5 (m, 2H), 7.3-7.4 (m, 2H), 7.0 (d, 2H, J=8.6 Hz), 6.8 (s, 1H), 4.1 (m, 4H), 3.90 (s, 3H), 3.5-3.8 (m, 3H), 2.3 (m, 2H), 1.5-2.1 (m, 8H).

LCMS: m/z 526 (M$^+$+1).

EXAMPLE 6

To a solution of (2S)—N-[4-(5-bromopentyloxy)-5-methoxy-2-nitrobenzoyl]pyrrolidine-2-carboxaldehyde diethylthioacetal 2b (549 mg, 1 mmol) in acetone (10 mL) was added anhydrous K₂CO₃ (552 mg, 4 mmol) and the 4-(1,3-benzoxazol-2-yl)-2-methoxyphenol 3d (241 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (1:1) as eluant to afford pure compound of 4f (522 mg, 75%).

$^1$H NMR (CDCl₃): δ 7.62-7.8 (m, 3H), 7.63 (s, 1H), 7.52 (m, 1H), 7.3 (m, 2H), 6.95 (d, 1H, J=8.5 Hz), 6.75 (s, 1H), 4.82 (d, 1H, J=3.8 Hz), 4.65 (m, 1H), 4.1 (m, 4H), 4.0 (s, 3H), 3.94 (s, 3H), 3.2 (m, 2H), 2.6-2.8 (m, 4H), 1.6-2.3 (m, 10H), 1.35 (q, 6H, J=7.6 Hz).

To compound 4f (695 mg, 1 mmol) in methanol (20 mL) was added SnCl₂.2H₂O (1.125 g, 5 mmol) and refluxed for 5 h or until the TLC indicated that reaction was completed. The methanol was evaporated under vacuum, the aqueous layer was then carefully adjusted to pH 8 with 10% NaHCO₃ solution and then extracted with ethyl acetate and chloroform (2×30 mL and 2×30 mL). The combined organic phase was dried over $Na_2SO_4$ and evaporated under vacuum to afford the crude amino diethylthioacetal 5f which was used directly in the next step.

A solution of 5f (679 mg, 1 mmol), $HgCl_2$ (613 mg, 2.26 mmol) and $CaCO_3$ (246 mg, 246 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $MeOH-CHCl_3$ (5%) to give compound 9f (278 mg, 50%). This material was repeatedly evaporated from $CHCl_3$ in vacuum to generate the imine form.

$^1$H NMR ($CDCl_3$): δ 7.7-7.84 (m, 3H), 7.62 (d, 1H, J=4.0 Hz), 7.43-7.58 (m, 2H), 7.3-7.4 (m, 2H), 6.9 (d, 1H, J=8.6 Hz), 6.8 (s, 1H), 3.9-4.2 (m, 10H), 3.5-3.7 (m, 3H), 1.6-2.3 (m, 10H).

LCMS: m/z 556 ($M^+$+1).

EXAMPLE 7

To a solution of 1 (400 mg, 1 mmol) in acetone (10 mL) was added anhydrous $K_2CO_3$ (552 mg, 4 mmol) and the 6a (389 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (3:2) as eluant to afford pure compound of 7a (496 mg, 70%).

$^1$H NMR ($CDCl_3$): δ 8.5 (s, 1H), 8.0 (m, 3H), 7.82 (d, 1H, J=7.6 Hz), 7.62 (m, 3H), 7.45 (t, 1H, J=7.6 Hz), 7.3 (t, 1H, J=7.6 Hz), 6.8 (s, 1H), 4.82 (d, 1H, J=3.8 Hz), 4.65 (m, 1H), 4.15 (m, 2H), 3.9 (s, 3H), 3.1-3.3 (m, 2H), 2.6-2.8 (m, 4H), 2.45 (m, 2H), 1.7-2.3 (m, 8H), 1.3 (q, 6H, J=6.8 Hz).

To compound 7a (709 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 8a which was used directly in the next step.

A solution of 8a (679 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $MeOH-CHCl_3$ (5%) to give compound 9g (277 mg, 50%). This material was repeatedly evaporated from $CHCl_3$ in vacuum to generate the imine form.

$^1$H NMR ($CDCl_3$): δ 8.8 (s, 1H), 8.05 (m, 3H), 7.9 (d, 1H, J=7.9 Hz), 7.7-7.8 (m, 3H), 7.6 (s, 1H), 7.3-7.5 (m, 2H), 6.9 (s, 1H), 4.2 (m, 2H), 3.9 (s, 3H), 3.5-3.8 (m, 3H), 2.6 (m, 2H), 1.6-2.3 (m, 8H).

LCMS: m/z 555 ($M^+$+1).

EXAMPLE 8

To a solution of 1 (400 mg, 1 mmol) in acetone (10 mL) was added anhydrous $K_2CO_3$ (552 mg, 4 mmol) and the 6b (407 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (3:2) as eluant to afford pure compound of 7b (545 mg, 75%).

$^1$H NMR ($CDCl_3$): δ 8.7 (bs, 1H), 7.9 (m, 3H), 7.7 (m, 3H), 7.5 (dd, 1H, J=2.3, 7.8 Hz), 7.1-7.2 (m, 1H), 6.8 (s, 1H), 4.8 (d, 1H, J=3.9 Hz), 4.7 (m, 1H), 4.1 (m, 2H), 3.9 (s, 3H), 3.2-3.3 (m, 2H), 2.7-2.8 (m, 4H), 2.45 (m, 2H), 1.8-2.3 (m, 8H), 1.2-1.4 (m, 6H).

LCMS: m/z 727 ($M^+$).

To compound 7b (727 mg, 1 mmol) in methanol (20 mL) was added $SnCl_2.2H_2O$ (1.125 g, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 8b, which was used directly in the next step.

A solution of 8b (697 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $MeOH-CHCl_3$ (5%) to give compound 9h (286 mg, 50%). This material was repeatedly evaporated from $CHCl_3$ in vacuum to generate the imine form.

$^1$H NMR ($CDCl_3$): δ 8.8 (bs, 1H), 7.95 (m, 3H), 7.6 (m, 3H), 7.7-7.8 (m, 2H), 7.1 (m, 1H), 6.7 (s, 1H), 4.1 (m, 2H), 3.8 (s, 3H), 3.4-3.75 (m, 3H), 2.5 (m, 2H), 1.6-2.3 (m, 8H).

LCMS: m/z 573 ($M^+$+1).

Biological Activity:
DNA Binding Affinity of Novel Benzothiazole, Benzoxazole Linked PBD Hybrids (9a-h):

Compounds have been subjected to thermal denaturation studies with duplex-form calf thymus DNA (CT-DNA) using a modification of a reported procedure (Newman, M. S. Carcinog-compr. Surv. 1976, 1, 203; (b) Hecht, S. S.; Loy, M.; Hoffman, Carcinog-compr. Surv. 1976, 1, 325). Working solutions in aqueous buffer (10 mM $NaH_2PO_4/Na_2HPO_4$, 1 mM $Na_2EDTA$, pH 7.00±0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 nm using a Beckman DU-800 spectrophotometer fitted with high performance temperature controller, and heated at 1° C. $min^{-1}$ in the 40-110° C. range. DNA helix→coil transition temperatures ($T_m$) have been obtained from the maxima in the d($A_{260}$)/dT derivative plots. Drug-induced alterations in DNA melting behavior are given by: $\Delta T_m = T_m(DNA+PBD) - T_m(DNA$ alone), where the $T_m$ value for the PBD-free CT-DNA is 69.1±0.01. The fixed [PBD]/[DNA] ratio used has not resulted in binding saturation of the host DNA duplex for any compound examined.

The DNA binding activity for these novel C8-linked benzothiazole, benzoxazole-PBD hybrids has been examined by thermal denaturation studies using calf thymus (CT) DNA. Melting studies show that these compounds stabilize the thermal helix→coil or melting stabilization ($\Delta T_m$) for the CT-DNA duplex at pH 7.0, incubated at 37° C., where PBD/DNA molar ratio is 1:5. The data for the compounds 9a-h is included in Table 1 for comparison.

TABLE 1

Thermal denaturation data for benzothiazole and benzoxazle linked PBD hybrids with calf thymus (CT) DNA

| PBD hybrids | [PBD]:[DNA] molar ratio[b] | ($\Delta T_m$ ° C.)[a] after incubation at 37° C. for | |
|---|---|---|---|
| | | 0 h | 18 h |
| 9a | 1:5 | 0.5 | 0.5 |
| 9b | 1:5 | 0.5 | 0.5 |
| 9c | 1:5 | 4.1 | 4.3 |
| 9d | 1:5 | 6.2 | 6.3 |
| 9e | 1:5 | 0.5 | 0.5 |
| 9f | 1:5 | 2.1 | 4.2 |
| 9g | 1:5 | 4.1 | 4.3 |
| 9h | 1:5 | 4.2 | 2.3 |
| DC-81 | 1:5 | 0.3 | 0.7 |

[a]For CT-DNA alone at pH 7.00 ± 0.01, $T_m$ = 69.1° C. ± 0.01 (mean value from 10 separate determinations), all $\Delta T_m$ values are ± 0.1-0.2° C.
[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

Anticancer activity: In vitro biological activity studies were carried out at the National Cancer Institute (USA).

The compounds were evaluated for in vitro anticancer activity against sixty human tumour cells derived from nine cancer types (leukemia, non-small-cell lung, colon, CNS, melanoma, ovarian, prostate, and breast cancer) as shown in Table 3. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$ TGI and $\log_{10}$ LC50 as well as $\log_{10}$ GI50 for 9a, 9b, 9c and 9d are listed in Table 2. As demonstrated by mean graph pattern, compound 9d exhibits an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 2

$\log_{10}$GI50 $\log_{10}$TGI and $\log_{10}$LC50 mean graphs midpoints (MG_MID) of in vitro cytotoxicity data for the representative compounds against human tumour cell lines

| Compound | $\log_{10}$GI50 | $\log_{10}$TGI | $\log_{10}$LC50 |
|---|---|---|---|
| 9a | −6.30 | −5.63 | −4.75 |
| 9b | −6.07 | −5.47 | −4.67 |
| 9c | −6.15 | −5.30 | −4.35 |
| 9d | −7.09 | −5.78 | −4.37 |

TABLE 3

$\log_{10}$ GI50 (concentration in mol/L) values for the representative compounds 9a-d

| Cancer | 9a | 9b | 9c | 9d |
|---|---|---|---|---|
| Leukemia | −6.73 | −6.40 | −6.65 | −7.51 |
| Non-small-cell-lung | −6.12 | −5.91 | −6.07 | −7.02 |
| Colon | −6.38 | −6.12 | −6.17 | −7.08 |
| CNS | −6.20 | −5.99 | −5.95 | −7.00 |
| Melanoma | −6.10 | −5.93 | −6.16 | −7.08 |
| Ovarian | −6.08 | −5.85 | −5.87 | −6.79 |
| Renal | −6.33 | −6.07 | −6.10 | −6.96 |
| Prostate | −6.55 | −6.45 | −6.54 | −7.47 |
| Breast | −6.43 | −6.19 | −6.28 | −7.25 |

Each cancer type represents the average of six to nine different cancer cell lines.

We claim:
1. A compound of formula 9

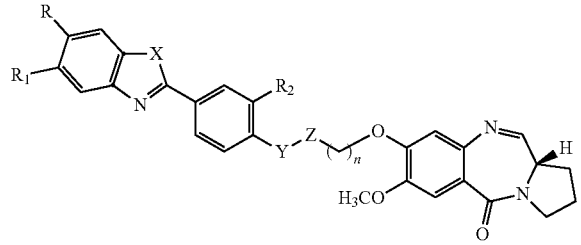

Formula 9 wherein: n=3-4, X=S or O; Y=NH or O; Z=CO or CH$_2$; R, R$_1$=H or F; R$_2$=OCH$_3$ or H.

2. The compound according to claim 1, selected from the group consisting of:
7-Methoxy-8-{4-[4-(1,3-benzothiazol-2-yl)phenoxy]butyl}oxy-(11aS)-1,2,3,11a-tetrahydro-5H-pyrrolo[2,1-c][1,4]benzodiazepin-5-one (9a);
7-Methoxy-8-{4-[4-(1,3-benzothiazol-2-yl)-2-methoxyphenoxy]butyl}oxy-(11aS)-1,2,3,11a-tetrahydro-5H-pyrrolo[2,1c-][1,4]benzodiazepin-5-one (9b);
7-Methoxy-8-{S-[4-(1,3-benzothiazol-2-yl)phenoxy]pentyl}oxy-(1aS)-1,2,3,11a-tetrahydro-5H-pyrrolo[2,1-c][1,4]benzodiazepin-5-one (9c);
7-Methoxy-8-{S-[4-(1,3-benzothiazol-2-yl)-2-methoxyphenoxy]pentyl}oxy(11aS)-1,2,3,11a-tetrahydro-5H-pyrrolo[2,1-c][1,4]benzodiazepin-5-one (9d);
7-Methoxy-8-{S-[4-(1,3-benzoxazol-2-yl)phenoxy]pentyl}oxy-(11aS) 1,2,3,11a-tetra-hydro-SH-pyrrolo[2,1-c][1,4]benzodiazepin-5-one (9e);
7-Methoxy-8-{S-[4-(1,3-benzoxazol-2-yl)-2-methoxyphenoxy]pentyl}oxy-(11as) 1,2,3,11a-tetra-hydro-5H-pyrrolo[2,1-c][1,4]benzodiazepin-5-one (9f);
7-Methoxy-8-{5-[N$^1$-(4-(1,3-benzothiazol-2-yl)phenyl)]pentanecarboxamide}oxy-(11aS)-1,2,3,11a-tetra-hydro-5H-pyrrolo[2,1-c][1,~]benzodiazepin-S-one (9g); and
7-Methoxy-8-{5-[N$^1$-(4-(6-fluoro-1,3-benzothiazol-2-yl)phenyl)]pentane carboxamide}oxy-(11aS)-1,2,3,11a-tetra-hydro-5H-pyrrolo[2,1-c][1,4], benzodiazepin-5-one (9h).

3. The compound according to claim 2, 7-methoxy-8-{4-[4-(1,3-benzothiazol-2-yl)phenoxy]butyl}oxy-(11aS)-1,2,3,11a-tetrahydro-5H-pyrrolo[2,1-c][1,4]benzodiazepin-5-one, which compound exhibits in-vitro cytotoxicity in mean graph midpoint value of −6.30(mol/lit), −S.63(mol/lit), and −4.7S (mol/lit) for $\log_{10}$ GI50, $\log_{10}$ TGI and $\log_{10}$ LC50, respectively, against nine human 'tumor cell lines selected from the group consisting of leukemia, non small-cell lung cancer, colon cancer, melanoma, renal cancer, ovarian cancer, prostate cancer and breast cancer.

4. The compound according to claim 2, 7-methoxy-8-{4-[4-(1,3-benzothiazol-2-yl)-2-methoxyphenoxy]butyl}oxy-(11aS)-1,2,3,11a-tetrahydro-5H-pyrrolo[2,1-c][1,4]benzodiazepin-5-one, which compound exhibits in vitro cytotoxicity in mean graph midpoint value of $\log_{10}$ TGI and $\log_{10}$ LC50, $\log_{10}$ GI50 of −6.07, −5.47, and −4.67 for $\log_{10}$ GI50, $\log_{10}$ TGI and $\log_{10}$ LC50, respectively, against nine human tumor cell lines selected from the group consisting of leukemia, non small-cell lung cancer, colon cancer, melanoma, renal cancer, ovarian cancer, prostate cancer and breast cancer.

5. The benzothiazole or benzoxazole linked pyrrolo[2,1-c][1,4]benzodiazepine according to claim 2, 7-methoxy-8-{S-[4-(1,3-benzothiazol-2-yl)phenoxy]pentyl}oxy-(11aS)-1,2,3,11a-tetrahydro-5H-pyrrolo[2,1-c][1, 4]benzodiazepin-5-one which compound exhibits invitro cytotoxicity in mean graph midpoint value of −6.1S, −S.30, and −4.35 for $\log_{10}$ GI50, $\log_{10}$ TGI and $\log_{10}$ LC50, respectively, against nine human tumor cell lines selected from the group consisting of leukemia, non small-cell lung cancer, colon cancer, melanoma, renal cancer, ovarian cancer, prostate cancer and breast cancer.

6. A process for the preparation of a compound of formula 9,

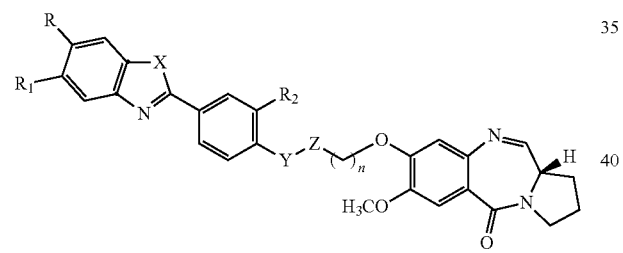

wherein: 'n' is 3-4, X=S, or O; Y=NH or O; Z=CO, or $CH_2$; R, $R_1$=H, or F;

$R_2$=$OCH_3$, or H and the said precess comprising the steps of:

a) reacting a compound of formula 1 or formula 2

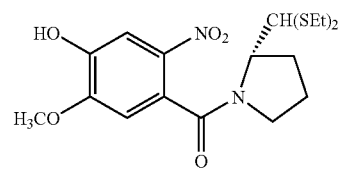

1

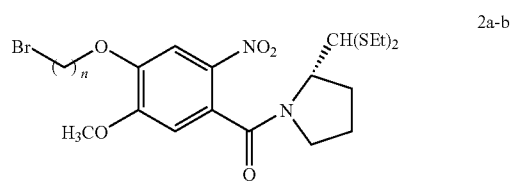

2a-b 2a (n = 3)
2b (n = 4)

with benzothiazole or benzoxazole derivative selected from the compounds of formula 3and 6,

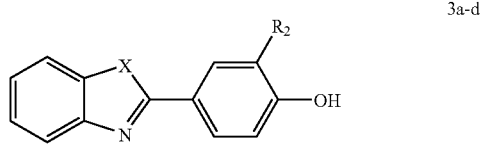

3a-d

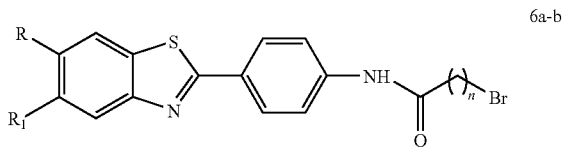

6a-b in the presence of $K_2CO_3$, in an organic solvent, under refluxing temperature to obtain the resultant nitro compound of formula 4 or 7;

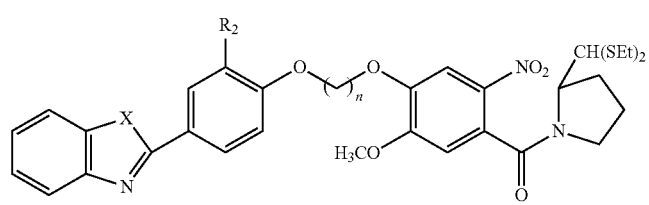

4a-f

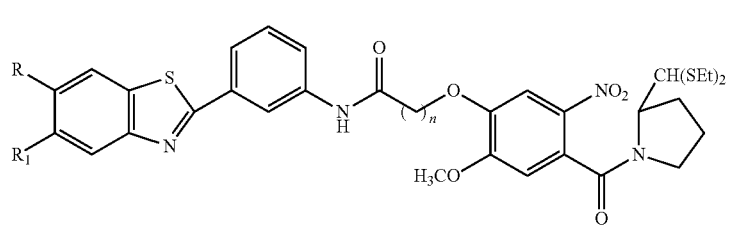

7a-b b) reducing the above said nitro compound of formula 4 or 7 obtained in step (a) with SnCl$_2$.2H$_2$O in an organic solvent, under reflux temperature and isolating the corresponding amino compound of formula 5 or 8, respectively, and

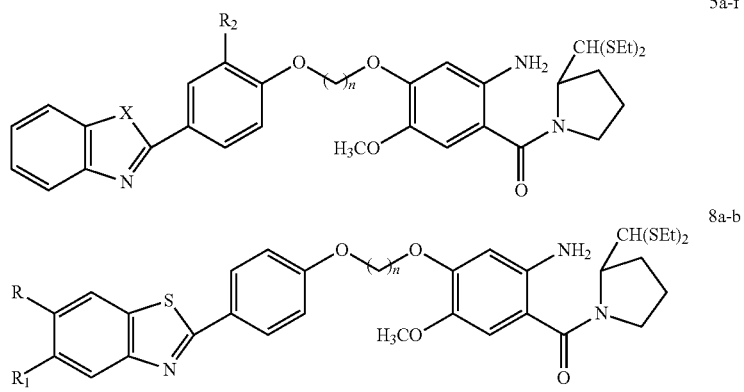

c) reacting the above said amino compound of formula 5 or 8 obtained in step (b) with a deprotecting agent by known method to obtain the desired compound of formula 9.

7. A process according to claim 6 wherein the organic solvent used in step (a) is acetone and in step (b) is ethanol or methanol.

8. A process according to claim 6, wherein in step (a) the compound of formula 2 is reacted with benzothiazole or benzoxazole derivative of formula 3 to obtain the resultant nitro compound of formula 4.

9. A process according to claim 6, wherein in step (a) the compound of formula 1 is reacted with benzothiazole or benzoxazole derivative of formula 6 to obtain the resultant nitro compound of formula 7.

10. A process according to claim 6, wherein the compound of formula 1 used in step (a) is (2S)—N-[4-hydroxy-5-methoxy-2-nitrobenzoyl]pyrrolidine-2-carboxaldehyde diethylthioacetal.

11. A process according to claim 6, wherein the compound of formula 2 used in step (a) is selected from (2S)—N-[4-(3-bromobutyl)oxy-5-methoxy-2-nitro benzoyl) pyrrolidine-2-carboxarbaldehyde diethylthioacetal (2a) and(2S)—N-[4-(5-bromopentyloxy)-5-methoxy-2-nitrobenzoyl]pyrrolidine-2-'carboxaldehyde diethylthioacetal (2b).

12. A process according to claim 6, wherein the compound of formula 3 obtained in step (a) is selected from the group consisting of 4-(benzothiazol-2-yl)phenol (3a), 4-(1,3-benzothiazol -2-yl)-2-methoxyphenol (3b), 4-(benzoxazol-2-yl)phenol (3e), and 4-(1,3-benzoxazol-2-yl)-2-methoxyphenol (3d).

13. A process according to claim 6, wherein the compound of formula 4 obtained in step (a) is selected from the group - consisting of (2S)—N-{4-(n-[4-(1,3-benzothiazol-2-yl)phenoxylbuty)oxy-5-methoxy-2-nitrobenzoyl}-pyrrolidine-2-carboxaldehyde diethylthioacetal (4a), (2S)—N-{4-(n-[4-(1,3-benzothiazol-2-yl)-2-methoxyphenoxy]butyl)oxy-5-methoxy-2-nitrobenzoyJ}-pyrrolidine-2-carbox aldehyde diethylthioacetal(4b), (2S)—N-{4-(n-[4-(1,3-benzothiazol-2-yl) phenoxy]penty)oxy-5-methoxy-2-nitrobenzoyl}-pyrrolidine-2-carboxaldehyde diethylthio acetal (4c),(2S)—N-{4-(n-[4-(1,3-benzothiazol-2-yl)-2-methoxy phenoxy] pentyl)oxy-5-methoxy-2-nitrobenzoyl}-pyrrolidine-2-carboxaldehyde diethylthioacetal (4d), (2S)—N-{4-(n-[4-(1,3-benzoxozol-2-yl)phenoxy[pentyl)oxy-5-methoxy-2-nitrobenzoyl}-pyrrolidine-2-carboxaldehyde diethylthioacetal (4e) and (2S)—N-{4-(n-[4-(1,3-benzoxozole-2-yl)-2-methoxyphenoxy]pentyt)oxy-5-methoxy-2-nitro benzoyl}-pyrrolidine -2-carboxaldehyde diethylthioacetal (4f).

14. A process according to claim 6, wherein the compound of formula 5 obtained in step (a) is selected from the group consisting of (2S)—N-{4-(n-[4-(1,3-benzo thiazol-2-yl)phenoxy]butyl)oxy-5-methoxy-2-aminobenzoyl}pyrrolidine-2-carboxaldehyde diethylthioacetal (5a), (2S)—N-{4-(n-[4-(1, 3-benzothiazol-2-yl)-2-methoxyphenoxy]butyl)oxy-5-methoxy-2-aminobenzoyl}-pyrrolidine -2-carbox aldehyde diethylthioacetal (5b), (2S)—N{4-(n-[4-(1,3-benzothiazol-2-yl)phenoxy]pentyl)oxy-5-methoxy-2-aminobenzoyl}-pyrrolidine-2-carboxaldehyde diethyl thioacetal (5c), (2S)—N{4-(n-[4-(1,3-benzothiazol-2-yl)-2-methoxy phenoxy] pentyl)oxy-5-methoxy-2-aminobenzoyl}-pyrrolidine-2-carboxaldehyde diethyl thioacetal (5d), (2S)N-{4-(n-[4-(1,3-benzoxozol-2-yl)phenoxy]benty)oxy-5-methoxy-2-aminobenzoyl}-pyrrolidine-2-carboxaldehyde diethylthioacetal (5e) and (2S)N-{4-(n-[4-(1,3-benzxozole-2-yl)-2-methoxyphenoxy]pentyl)oxy-5-methoxy-2-aminobenzoyl}-pyrrolidine-2-carboxaldehyde diethylthioacetal (5f).

15. A process according to claim 6, wherein the compound of formula 6 used in step (a) is selected from N1-[4-(1,3-benzothiazol-2-yl)phenyl]-5-bromopentanamide (6a) or N1-[4-(6-fluoro-1,3-benzothiazol-2-yl)phenyl]-5-bromopentanamide (6b).

16. A process according to claim 6, wherein the compound of formula 7 obtained in step (a) is selected from (2S)—N-{4-(5-[N$^1$-(4-(1, S-benzothiazol . . . , 2-yl)phenyl)]-pentanecarboxamide)oxy-5-methoxy-2-nitrobenzoyl}-pyrrolidine-2-carboxaldehyde diethylthioacetal (7a) or (2S)—N-{4-(5-[N$^1$-(4-(6-fluoro-1,3-benzothiazol-2-yl)phenyl)-pentanecarboxamide]oxy)-5-methoxy-2-nitrobenzoyl}-pyrrolidine-2-carboxaldehyde diethylthioacetal (7b).

17. A process according to claim 6, wherein the compound of formula 8 obtained is selected from the group consisting of (2S)—N-{4-(n-(4-(1,3-benzothiazol-2-yl)phenoxy]butyJ) oxy-5-methoxy-2-aminobenzoyl}pyrrolidine-2-carbox aldehyde diethyl thioacetal (8a) and (2S)—N-{4-(n-[4-(1,3-benzothiazol-2-yl)-2-methoxyphenoxy]pentyl) oxy-5-methoxy-2-aminobenzoyl}-pyrrolidine-2-carboxaldehyde diethylthioacetal (8b).

\* \* \* \* \*